United States Patent [19]

Mulhauser

[11] Patent Number: 4,754,087

[45] Date of Patent: Jun. 28, 1988

[54] PROCESS FOR THE PREPARATION OF PRIMARY TERTIARY ALLYL HALIDES

[75] Inventor: Michel Mulhauser, Ecully, France

[73] Assignee: Rhone-Poulenc Sante, Courbevoie, France

[21] Appl. No.: 777,848

[22] Filed: Sep. 19, 1985

[30] Foreign Application Priority Data

Sep. 20, 1984 [FR] France .................. 84 14425

[51] Int. Cl.$^4$ .................. C07C 17/08; C07C 17/00
[52] U.S. Cl. ..................... 570/231; 570/238
[58] Field of Search .......................... 570/231

[56] References Cited

U.S. PATENT DOCUMENTS

| | | | |
|---|---|---|---|
| 2,609,388 | 9/1952 | Knapp et al. | 570/231 |
| 3,318,945 | 5/1967 | Erman | 570/231 |
| 3,400,162 | 9/1968 | Beets et al. | 570/231 |
| 3,812,212 | 5/1974 | Gordon | 570/249 |
| 3,993,586 | 11/1976 | Hagedorn et al. | 570/231 |
| 4,168,271 | 9/1979 | Cardenas et al. | 570/189 |
| 4,214,098 | 7/1980 | deJong et al. | 570/231 |
| 4,704,485 | 11/1987 | Mitchell et al. | 570/231 |
| 4,704,486 | 11/1987 | McElligott | 570/231 |

FOREIGN PATENT DOCUMENTS 132542  2/1985  European Pat. Off. ............ 570/231

*Primary Examiner*—J. E. Evans
*Attorney, Agent, or Firm*—Stevens, Davis, Miller & Mosher

[57] ABSTRACT

Primary and/or tertiary allyl halides are prepared by reaction of a hydrogen halide (e.g. hydrogen chloride) with a terminal conjugated diene (e.g. myrcene, β-farnesene, β-springene or 15-chloro-β-springene) in the presence of, as catalyst, a cuprous halide together with a quaternary ammonium salt or a phosphonium salt containing at most 16 carbon atoms, or a salt of a tertiary amine containing at most 10 carbon atoms, the reaction being carried out in an organic solvent in which the catalyst complex is soluble.

12 Claims, No Drawings

PROCESS FOR THE PREPARATION OF PRIMARY TERTIARY ALLYL HALIDES

The present invention relates to the preparation of primary and/or tertiary allyl halides by reaction of a hydrogen halide with a terminal conjugated diene.

Numerous processes for the hydrohalogenation of conjugated dienes are known but these processes have the major disadvantage that they are of low selectivity. More especially, the hydrohalogenation of myrcene can result in the production of a mixture of halides as shown in the following reaction scheme:

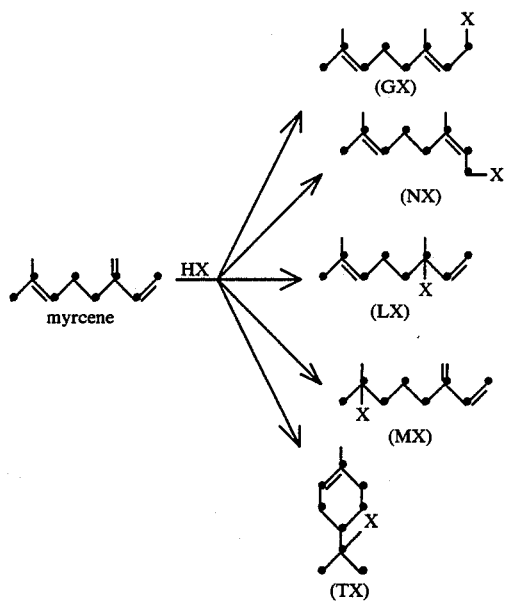

wherein
X represents chlorine or bromine,
GX is a geranyl halide,
NX is a neryl halide,
LX is a linalyl halide,
MX is a myrcenyl halide and
TX is a terpenyl halide.

The mixture of these different halides in varying proportions is commonly referred to as myrcene hydrobromide or myrcene hydrochloride.

According to U.S. Pat. No. 3,031,442, the hydrochlorination of pure myrcene in the presence of cuprous chloride gives a mixture of geranyl and neryl chlorides (75 to 80%), linalyl chloride (5 to 10%) and terpenyl chloride (10 to 15%).

Under the conditions described in U.S. Pat. No. 3,413,364 the hydrochlorination of 75.8% pure myrcene in the presence of mercuric chloride gives a mixture of geranyl and neryl chlorides (2%), linalyl chloride (5%), myrcenyl chloride (77%) and terpenyl chloride (16%).

According to U.S. Pat. No. 3,016,408, the hydrochlorination or hydrobromination of technical-grade myrcene in the presence of cupric acetate gives a mixture of geranyl and neryl halides (30 to 35%), linalyl halide (40 to 49%), myrcenyl halide (0 to 10%) and terpenyl halide (15 to 18%).

European Patent Application EP No. 132,544, published on 13th Feb. 1985, describes the hydrohalogenation of a conjugated diene, in particular myrcene, in the presence of a catalyst based on copper and on a quaternary ammonium salt or phosphonium salt containing at least 18 carbon atoms. The quaternary ammonium salt or phosphonium salt allows the catalyst to dissolve in the myrcene. However, it is difficult to separate the catalyst system from the reaction products because the quaternary ammonium salts and the phosphonium salts, as defined in European Patent Application EP No. 132,544, cannot easily be removed by, for example, washing the reaction mixture with water.

In view of the value of myrcene in the synthesis of vitamins A and E and of terpene products such as citral or linalyl acetate it is of particular interest to have available a selective process for the production of geranyl, neryl and linalyl halides which, having regard to their labile nature, permits their easy separation from the reaction mixture.

It has now been found, and it is this which forms the subject of the present invention, that the hydrohalogenation of terminal conjugated dienes takes place selectively and with good yields when there is used a hydrogen halide, preferably hydrogen chloride, in the presence of a catalyst consisting of a cuprous halide, such as cuprous chloride or cuprous iodide, together with a quaternary ammonium salt or a phosphonium salt containing at most 16 carbon atoms or a salt of a tertiary amine containing at most 10 carbon atoms, the reaction being carried out in an organic solvent capable of dissolving the catalyst system, preferably an aliphatic halogenated hydrocarbon such as methylene chloride, or an organic acid or organic acid anhydride, such as acetic acid or acetic anhydride, or a mixture thereof.

The process is generally carried out at a temperature below 20° C. and preferably below 0° C.

Moreover, to avoid the formation of polyhalogenated products it is particularly advantageous to use the hydrogen halide in the stoichiometric amount relative to the conjugated diene employed.

In general, in carrying out the process of the invention, a cuprous halide is used in a molar ratio of 0.05 to 10%, preferably 0.1 to 3%, relative to the conjugated diene employed, together with a quaternary ammonium salt or a phosphonium salt in a molar ratio of 0.05 to 10%, preferably 0.1 to 3%, relative to the conjugated diene.

The quaternary ammonium salts and the phosphonium salts may be chosen from among the tetraalkylammonium halides or tetraalkylphosphonium halides containing at most 16 carbon atoms, such as the tetra-n-butylammonium or tetra-n-butylphosphonium chlorides or bromides. The salts of tertiary amines may be chosen from among the hydrohalides of trialkylamines containing at most 10 carbon atoms, such as triethylamine hydrochloride.

The mixture of the primary and/or tertiary allyl halides obtained in accordance with the process of the present invention can be separated from the reaction mixture, after it has been washed with water to remove the catalyst system by dissolving it in the aqueous phase, using an organic solvent, preferably an aliphatic hydrocarbon (e.g. pentane or hexane) or an aromatic hydrocarbon (e.g. benzene). The hydrohalogenation products are obtained after evaporation of the organic phase, and can be purified by distillation.

In particular, in the case of myrcene, the process of the invention makes it possible to obtain geranyl chloride and neryl chloride in yields which are generally greater than those obtained in accordance with the previously known processes.

The process according to the present invention is particularly suitable for carrying out the hydrochlorination of terminal conjugated dienes possessing terpene chains such as myrcene, β-farnesene, β-springene or 7,11,15-trimethyl-3-methylene-15-chloro-1,6,10-hexadecatriene (or 15-chloro-β-springene), the allyl halides of which can be converted into, for example, vitamin E in accordance with the known methods described in the literature.

The examples which follow show how the invention may be put into practice.

EXAMPLE 1

Tetra-n-butylammonium chloride (1.9 g=0.00685 mole) is introduced, under an argon atmosphere into a 250 cc three-neck flask equipped with a magnetic stirrer, a thermometer, a tube extending down to the level of the stirrer and a hydrogenation head, and is dried by heating to a temperature of between 90° and 100° C. for 2 hours under reduced pressure. After cooling to 40° C., anhydrous methylene chloride (75 cc) and cuprous chloride (0.675 g=0.00682 mole) are introduced rapidly. The mixture is stirred under an argon atmosphere until the cuprous chloride has dissolved. This gives a homogeneous yellow solution which is cooled to a temperature of between −3° and −5° C. Myrcene (37.2 g=0.274 mole), which is more than 95% pure, is then added, followed by dry hydrogen chloride (10 g=0.274 mole) in the course of 3 hours 15 minutes. The homogeneous solution turns brown. The reaction mixture is poured into an aqueous solution (200 cc) of ammonium chloride (100 g/liter). The organic phase is separated off and the aqueous phase is then extracted with methylene chloride (100 cc). The combined organic phases are washed with water (3×50 cc) and then dried over potassium carbonate. After filtration and evaporation of the solvent, the residue obtained is taken up in pentane (100 cc); tetra-n-butylammonium chloride precipitates. After filtration, the solvent is evaporated under reduced pressure. This gives, in a yield of 90.4%, a slightly yellow oil (42.7 g), of which the analysis by vapour phase chromatography (VPC) and by nuclear magnetic resonance (NMR) shows that it consists of:

|  | VPC | NMR |
| --- | --- | --- |
| geranyl and neryl chlorides | 85.4% | 87% |
| linalyl chloride | 5.4% | 6% |
| myrcenyl chloride | 0.2% |  |
| terpenyl chloride | 2% | 3% |
| myrcene | 3.3% | 4% |
| C<sub>10</sub> dihydrochlorinated hydrocarbons | 2.1% |  |
| C<sub>10</sub> hydrocarbons (other than myrcene) | 1% |  |

The degree of conversion of myrcene is about 97% and the yield of geranyl, neryl and linalyl chlorides is about 77.5%.

EXAMPLE 2

Triethylamine hydrochloride (2.01 g), methylene chloride (100 cc) and cuprous chloride (1.45 g) are introduced, under an argon atmosphere, into a 500 cc three-neck flask equipped with a magnetic stirrer, a thermometer a tube extending to the level of the stirrer and a hydrogenation head. The mixture is stirred at a temperature of 20° C. until the cuprous chloride has dissolved, and is then cooled to −10° C. Myrcene (100 g) which is more than 95% pure is then added followed, over the course of 2 hours, by anhydrous hydrogen chloride (26.8 g), while keeping the temperature between −9° and −11° C.

The solution obtained is poured into a 10% strength aqueous ammonium chloride solution (200 cc). The organic products are extracted with pentane (200 cc). The organic phase is washed with water and then dried over potassium carbonate. After evaporation of the solvents under reduced pressure, an oil (128.1 g) is obtained, analysis of which by vapour phase chromatography shows that it consists of:

| geranyl and neryl chlorides | 81.5% |
| --- | --- |
| linalyl chloride | 6.15% |
| terpenyl chloride | 1.2% |
| myrcene | 0.95% |
| C<sub>10</sub> dihydrochlorinated hydrocarbons | 1.7% |

The degree of conversion of myrcene is about 99%.

EXAMPLE 3

Following the procedure in Example 2, but using 1 mole of myrcene and adding the hydrogen chloride at a temperature of between −14° and −16° C., an oil (173.6 g) having the following composition is obtained:

| geranyl and neryl chlorides | 86.8% |
| --- | --- |
| linalyl chloride | 5.9% |
| myrcenyl chloride | 0.2% |
| terpenyl chloride | 1.6% |
| myrcene | 1.6% |
| C<sub>10</sub> dihydrochlorinated hydrocarbons | 1.1% |
| C<sub>10</sub> hydrocarbons (other than myrcene) | 2.3% |

The degree of conversion of myrcene is about 98.4% and the yield of geranyl, neryl and linalyl chlorides is 85.2%.

EXAMPLE 4

The procedure described in Example 2 is followed, but using a molar ratio of cuprous chloride and tetra-n-butylammonium chloride of 0.5% (instead of 2.5%) relative to the myrcene employed and adding the hydrogen chloride at a temperature of between −14° and −16° C. An oil having the following composition is obtained:

| geranyl and neryl chlorides | 71% |
| --- | --- |
| linalyl chloride | 11.8% |
| myrcenyl chloride | 0.4% |
| terpenyl chloride | 4.1% |
| myrcene | 7% |
| C<sub>10</sub> dihydrochlorinated hydrocarbons | 1.3% |
| C<sub>10</sub> hydrocarbons (other than myrcene) | 3.5% |

EXAMPLE 5

The procedure described in Example 2 is followed using:

| myrcene | 37.24 g (0.274 mole) |
| --- | --- |
| dry hydrogen chloride | 10.0 g (0.274 mole) |
| cuprous chloride | 2.7 g (0.0274 mole) |
| tetra-n-butylammonium chloride | 7.6 g (0.0274 mole) |
| methylene chloride | 75 cc |

The dry hydrogen chloride is added over the course of 30 minutes at a temperature of between −3° and −5° C.

After treatment of the reaction mixture, an oil (47.42 g) having the following composition is obtained:

|  | VPC | NMR |
|---|---|---|
| geranyl and neryl chlorides | 82.3% | 84% |
| linalyl chloride | 4.7% | 6% |
| terpenyl chloride | 3.4% | 6% |
| myrcene | 2.3% | 4% |
| $C_{10}$ hydrochlorinated hydrocarbons | 0.5% | |
| $C_{10}$ dihydrochlorinated hydrocarbons | 2.8% | |
| $C_{10}$ hydrocarbons (other than myrcene) | 3.6% | |

EXAMPLE 6

Triethylamine hydrochloride (1.4 g=0.01 mole; 2.5 mole% relative to the myrcene employed) and methylene chloride (120 cc) are introduced, under an argon atmosphere into an apparatus identical to that described in Example 2. Cuprous chloride (1 g=0.01 mole; 2.5 mole% relative to the myrcene employed) is then added. The mixture is stirred until a homogeneous yellow solution is obtained, which is cooled to −5° C. Myrcene (56 g=0.41 mole) which is more than 95% pure is added, followed by dry hydrogen chloride (15 g=0.41 mole) over the course of 5 hours. After treatment of the reaction mixture under the conditions of Example 2, an oil (68.8 g) having the following composition is obtained:

| geranyl and neryl chlorides | 88.1% |
|---|---|
| linalyl chloride | 5.1% |
| terpenyl chloride | 1.9% |
| myrcene | 3.7% |
| $C_{10}$ hydrochlorinated hydrocarbons | 0.2% |
| $C_{10}$ dihydrochlorinated hydrocarbons | 0.4% |
| $C_{10}$ hydrocarbons (other than myrcene) | 0.6% |

The degree of conversion of myrcene is 97% and the yield of geranyl, neryl and linalyl chlorides isolated is 88%.

EXAMPLE 7

The procedure described in Example 6 is followed, but using technical-grade myrcene having the following composition:

| myrcene | 68.3% |
|---|---|
| β-pinene | 6.8% |
| limonene | 9.3% |
| other $C_{10}$ hydrocarbons | 7.9% |

Anhydrous hydrogen chloride (20 g) is introduced, in the course of 4 hours 30 minutes at −5° C., into a solution of technical-grade myrcene (103.8 g) in methylene chloride (160 cc) containing a catalyst consisting of an equimolecular mixture of cuprous chloride and triethylamine hydrochloride (2.5 mole% relative to the myrcene). After treatment of the reaction mixture, an oil is obtained, analysis of which shows that the degree of conversion of myrcene is 92% and the yield of geranyl, neryl and linalyl chlorides is 91% relative to the myrcene converted.

EXAMPLE 8

Triethylamine hydrochloride (0.48 g; 10 mole% relative to β-springene), methylene chloride (15 cc), acetic acid (10 cc) and cuprous chloride (90 mg=2.5 mole% relative to β-springene) are introduced, under an argon atmosphere, into an apparatus identical to that described in Example 2. The reaction mixture is stirred until a homogeneous solution is obtained. This is cooled to −10° C. and β-springene (10 g=0.0367 mole) (obtained by condensing geranyl-magnesium chloride with 3-chloromyrcene under the conditions described in U.S. Pat. No. 4,292,459) is then added, followed, over the course of 1 hour, by dry hydrogen chloride gas (1.3 g). After treatment of the reaction mixture under the conditions described above, a pale yellow oil (10.9 g; 96.5% of theory) is obtained, the mass spectrum and proton nuclear magnetic resonance spectrum of which agree with the structure of the expected product.

This oil (2 g) is catalytically hydrogenated in the presence of 10% strength palladium-on-charcoal (200 mg) in ethanol (20 cc) under a pressure of 50 bars for 4 hours.

The chromatogram found by capillary gas phase chromatography of the product obtained is identical to that of the product obtained by hydrogenating β-springene to phytane under the same conditions.

EXAMPLE 9

The procedure of Example 2 is followed, using:

| myrcene (more than 95% pure) | 50 g (0.367 mole) |
|---|---|
| cuprous chloride | 1.82 g (0.0184 mole) |
| triethylamine hydrochloride | 2.53 g (0.0250 mole) |
| acetic anhydride | 66 cc |
| acetic acid | 33 cc |

The hydrogen chloride (13.4 g=0.367 mole) is added over the course of 3 hours at −10° C.

After treatment of the reaction mixture, an oil is obtained, analysis of which by vapour phase capillary chromatography shows that it consists of:

| geranyl and neryl chlorides | 63.6% |
|---|---|
| linalyl chloride | 5% |
| myrcenyl chloride | 1% |
| terpenyl chloride | 2.8% |
| myrcene | 22.9% |
| $C_{10}$ dihydrochlorinated hydrocarbons | 1.9% |
| $C_{10}$ hydrocarbons (other than myrcene) | 2.6% |

The degree of conversion of myrcene is 81% and the yield of geranyl, neryl and linalyl chlorides is 89% relative to the myrcene converted.

EXAMPLE 10

The procedure followed is as in Example 8, but the hydrochlorination is carried out on 7,11,15-trimethyl-3-methylene-15-chloro-hexadeca-1,6,10-triene (or 15-chloro-β-springene) (6.3 g=0.02 mole). 1,15-dichloro-3,7,11,15-tetramethyl-hexadeca-2,6,10-triene is obtained, in a yield of 95%, in the form of a mixture of the E and Z forms, which is hydrogenated to phytane with a selectivity of 98%.

The 7,11,15-trimethyl-3-methylene-15-chloro-hexadeca-1,6,10-triene can be prepared as follows:

Magnesium (12.15 g), anhydrous tetrahydrofuran (30 cc) and a crystal of iodine are introduced into a 250 cc reactor. The mixture is cooled to −20° C. and a solution of 1,7-dichloro-3,7-dimethyl-oct-2-ene (a mixture of the E and Z forms) (20.9 g) in anhydrous tetrahydrofuran (85 cc) is then added over the course of 5 hours 30 minutes. The mixture is stirred for 18 hours at −20° C. The excess magnesium is removed by filtering the reaction mixture in the absence of air and of humidity. The solution obtained is poured into a dropping funnel located on top of a reactor containing copper iodide (0.5 g) and tetrahydrofuran (5 cc). Some of the solution of the magnesium compound (1.5 cc) is run in, and 87% pure 3-chloro-myrcene (19.5 g) in tetrahydrofuran (10 cc) is then added rapidly.

The mixture is cooled to −20° C. and the whole of the solution of the magnesium compound is then run in over the course of 3 hours. The temperature is then allowed to return to about 20° C. The reaction mixture is taken up in an aqueous sodium chloride solution and is then extracted with pentane. The pentane solution is dried over magnesium sulphate. After filtration, and evaporation of the solvent, an oil (29.7 g) is obtained.

Analysis by gas phase chromatography shows that the degree of conversion of the 3-chloromyrcene is 69%.

The oil obtained is heated to 100°–105° C. under reduced pressure (0.5–1 mm Hg; 0.067–0.13 kPa) to remove the unreacted $C_{10}$ products. This gives a residue (20.0 g) which, according to the mass spectrum and proton nuclear magnetic resonance spectrum, contains 85% of 7,11,15-trimethyl-3-methylene-15-chloro-hexadeca-1,6,10-triene.

The yield is 82% relative to the 3-chloromyrcene consumed.

EXAMPLE 11

The procedure followed is as in Example 2, but using:

| | |
|---|---|
| myrcene (more than 95% pure) | 75 g |
| cuprous iodide | 2.62 g |
| triethylamine hydrochloride | 1.9 g |
| methylene chloride | 150 cc |
| dry hydrogen chloride | 20.2 g |

The hydrogen chloride is introduced over the course of 4 hours 30 minutes at a temperature of −8° C.

After treatment of the reaction mixture, an oil (93.3 g) is obtained, analysis of which by proton nuclear magnetic resonance shows that it consists of:

| | |
|---|---|
| geranyl and neryl chlorides | 90% (E/Z = 70/30) |
| linalyl chloride | 10% |
| terpenyl chloride | traces (less than 0.1%) |
| myrcene | traces (less than 0.1%) |

The yield is 98% by weight.

EXAMPLE 12

The procedure followed is as in Example 2, but using:

| | |
|---|---|
| myrcene (more than 95% pure) | 75 g |
| cuprous chloride | 1.36 g |
| tetra-n-butylphosphonium chloride | 4.05 g |
| methylene chloride | 150 cc |
| dry hydrogen chloride | 20.0 g |

The hydrogen chloride is introduced over the course of 4 hours at a temperature of −10° C.

After treatment of the reaction mixture, an oil (94.1 g) is obtained, analysis of which by proton nuclear magnetic resonance shows that it consists of:

| | |
|---|---|
| geranyl and neryl chlorides | 90% (E/Z = 60/40) |
| linalyl chloride | 10% |
| terpenyl chloride | traces (less than 0.1%) |
| myrcene | traces (less than 0.1%) |

The yield is 99% by weight.

EXAMPLE 13

Triethylamine hydrochloride (407 mg), cuprous chloride (131 mg), methylene chloride (6 cc) and acetic acid (6 cc) are introduced, under an argon atmosphere, into a three-neck flask. After 5 minutes' stirring at 20° C., a yellow solution is obtained. After cooling this to −10° C., 94% pure phytatriene (13 g) (obtained according to U.S. Pat. No. 4,292,459) dissolved in methylene chloride (10 cc) and acetic acid (10 cc) is added. Thereafter, anhydrous hydrogen chloride (1.6 g) is introduced over the course of 1 hour at a temperature of between −7° and −10° C. After completion of the addition of hydrogen chloride, stirring is continued for 2 hours at the same temperature. The reaction mixture is poured into a mixture of pentane (50 cc) and an aqueous solution (50 cc) of ammonium chloride (100 g/liter). After decanting, the organic phase is dried over sodium sulphate. After filtration and evaporation of the solvent, an oil (15.52 g) is obtained, analysis of which by proton nuclear magnetic resonance spectrometry and by mass spectrometry shows that it consists essentially of monohydrochlorophytatriene.

Hydrogenation of the oil obtained (3.5 g) dissolved in ethanol (30 cc) in the presence of 10% strength by weight palladium on charcoal (300 mg) under a hydrogen pressure of 30 bars for 4 hours at 20° C. gives phytane in a yield of 92% and with a selectivity of 98%.

I claim:

1. Process for the preparation of a primary and/or tertiary allyl halide which comprises reacting a hydrogen halide with a terminally conjugated diene under dry conditions and at a temperature below 20° C. in the presence of, as catalyst, a cuprous halide together with a quaternary ammonium salt or a phosphonium salt containing at most 16 carbon atoms, or a salt of a tertiary amine containing at most 10 carbon atoms, in an organic solvent capable of dissolving the catalyst said solvent being a halogenated aliphatic hydrocarbon, an organic acid, an organic acid anhydride, or a mixture of any of these, treating the reaction mixture with water and an organic solvent to remove the catalyst system in aqueous solution, and then separating the primary and/or tertiary allyl halides after removal of the solvent from the organic phase.

2. Process according to claim 1, in which the said solvent is methylene chloride, acetic acid, acetic anhydride or a mixture of any of these.

3. Process according to claim 1, in which the reaction is carried out at a temperature below 0° C.

4. Process according to claim 1, in which the cuprous halide is used in a molar ratio of 0.05 to 10% relative to the conjugated diene employed.

5. Process according to claim 1, in which the quaternary ammonium salt or phosphonium salt is used in a molar ratio of 0.05 to 10% relative to the conjugated diene employed.

6. Process according to claim 1, in which the hydrogen halide is hydrogen chloride.

7. Process according to claim 1, in which the quaternary ammonium salt or phosphonium salt containing at most 16 carbon atoms is a tetraalkylammonium halide or a tetraalkylphosphonium halide and the salt of a tertiary amine containing at most 10 carbon atoms is a trialkylamine hydrohalide.

8. Process according to claim 7, in which the quaternary ammonium salt, phosphonium salt or tertiary amine salt is tetra-n-butylammonium chloride or bromide, tetra-n-butylphosphonium chloride or bromide, or triethylamine hydrochloride.

9. Process according to claim 1, in which the cuprous halide is cuprous chloride or iodide.

10. Process according to claim 1, in which the primary and/or tertiary allyl halide is purified by distillation.

11. Process according to claim 1, in which the reaction mixture is washed, after the halogenation, with water and an aliphatic or aromatic hydrocarbon, and the primary and/or tertiary allyl halide is isolated after removal of the solvent.

12. Process according to claim 1, in which the terminally conjugated diene used as starting material is myrcene and the product is a mixture of geranyl chloride, neryl chloride and linalyl chloride.

* * * * *